United States Patent
Kostansek

(10) Patent No.: US 6,548,448 B2
(45) Date of Patent: Apr. 15, 2003

(54) DELIVERY SYSTEMS FOR CYCLOPROPENES

(75) Inventor: Edward Charles Kostansek, Buckingham, PA (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 10/083,172

(22) Filed: Feb. 26, 2002

(65) Prior Publication Data

US 2002/0198107 A1 Dec. 26, 2002

Related U.S. Application Data

(60) Provisional application No. 60/271,525, filed on Feb. 26, 2001.

(51) Int. Cl.[7] ........................ A01N 25/10; A01N 25/28; A01N 25/34; A01N 27/00

(52) U.S. Cl. ...................... 504/193; 206/423; 504/207; 504/326; 504/349; 504/351; 504/357; 47/65.7; 47/65.8; 47/66.7; 47/87

(58) Field of Search .......................... 206/423; 47/65.7, 47/65.8, 66.7, 87; 504/357, 193, 207, 326, 349, 351

(56) References Cited

U.S. PATENT DOCUMENTS

| | | | |
|---|---|---|---|
| 5,518,988 A | 5/1996 | Sisler et al. | 504/114 |
| 6,017,849 A | 1/2000 | Daly et al. | 504/114 |
| 6,426,319 B1 * | 7/2002 | Kostansek | 504/357 |

* cited by examiner

Primary Examiner—S. Mark Clardy
(74) Attorney, Agent, or Firm—Thomas D. Rogerson

(57) ABSTRACT

The present invention relates to new delivery systems for cyclopropenes in which the cyclopropene, either free or encapsulated within a molecular encapsulation agent is incorporated into produce packaging materials.

10 Claims, No Drawings

DELIVERY SYSTEMS FOR CYCLOPROPENES

CROSS REFERENCE TO RELATED PATENT APPLICATIONS

This is a non-provisional application of prior pending U.S. provisional application Ser. No. 60/271,525 filed Feb. 26, 2001.

The present invention relates to new delivery systems for cyclopropenes in which the cyclopropene, either free or encapsulated within a molecular encapsulation agent, is incorporated into packaging materials for agricultural produce and ornamental plants.

It is well known that ethylene can cause the premature death of plants or plant parts including, for example, flowers, leaves, fruits, and vegetables through binding with certain receptors in the plant. Ethylene is known to promote leaf yellowing and stunted growth as well as premature fruit, flower, and leaf drop. In addition, ethylene is also known to induce or accelerate the ripening of harvested fruits and vegetables. Because of these ethylene-induced problems, very active and intense research presently concerns the investigation of ways to prevent or reduce the deleterious effects of ethylene on plants. U.S. Pat. No. 5,518,988 discloses the use of cyclopropene and its derivatives, including methylcyclopropene, as effective blocking agents for ethylene binding. However, a major problem with these compounds is that they are typically unstable gases which present explosive hazards when compressed. U.S. Pat. No. 6,017,849 discloses a method of incorporating these gaseous compounds into a molecular encapsulation agent complex in order to stabilize their reactivity and thereby provide a convenient and safe means of storing, transporting and applying or delivering the active compounds to plants as a way to alleviate these problems. For the most active cyclopropene derivative disclosed in U.S. Pat. No. 5,518,988, 1-methylcyclopropene ("1-MCP"), the preferred molecular encapsulation agent is a cyclodextrin, with α-cyclodextrin being the most preferred. The application or delivery of these active compounds to plants is accomplished by simply adding water to the molecular encapsulation agent complex. The complex is prepared according to the methods disclosed in U.S. Pat. No. 6,017,849 which provides the material in the form of a powder.

The powdered complex is usually added to water to release the 1-MCP into the atmosphere where plants or plant parts to be treated are stored, that is, a treatment container or room. Typical treatment concentrations are 0.1 to 1.0 ppm (vol/vol) in the atmosphere surrounding the plant or plant parts. In order to accomplish this release large amounts of water are required, at least ten times and preferably twenty times the weight of the 1-MCP/α-cyclodextrin complex. It would advantageous to have a delivery system in which 1-MCP is incorporated into packaging materials which often surround plants or plant parts and in which 1-MCP is released without the need for adding water.

We have surprisingly found that the low concentrations of cyclopropenes needed to treat fruits, vegetables, and flowers ("produce") can be released from packaging materials which incorporate the cyclopropene. The cyclopropene can be incorporated directly into many types of packaging materials or it can first be encapsulated into a molecular encapsulation agent which is then subsequently incorporated into packaging materials. We have found that moisture from humid air surrounding produce is often sufficient to release the amounts of cyclopropene required for effective treatment of the produce. In one form of the invention the powdered complex is prepared as part of the film or container. The powder can be compounded within, or laminated between, different thermoplastic packaging plastics such as polyethylene, ethyl vinylacetate, polyvinyl alcohol or with rigid plastics such as polystyrene, polycarbonate, and polymethyl methacrylate. In addition, it can be incorporated into various waxes and coated papers and cardboard or it can be incorporated into an adhesive component of packaging materials.

The present invention is, therefore, a composition comprising a) a compound of the formula:

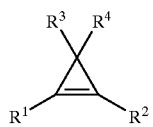

wherein:
1) each $R^1$, $R^2$, $R^3$, and $R^4$ is independently a group of the formula:

—(L)$_n$—Z wherein:
i) n is an integer from 0 to 12;
ii) each L is independently selected from a member of the group D, E or J wherein:
D is of the formula:

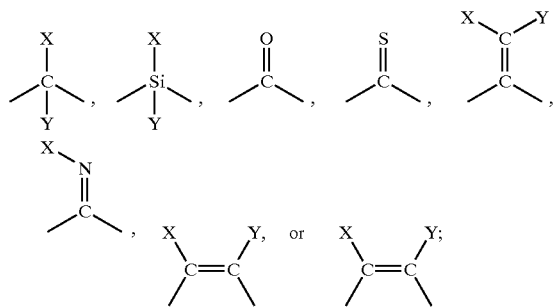

E is of the formula:

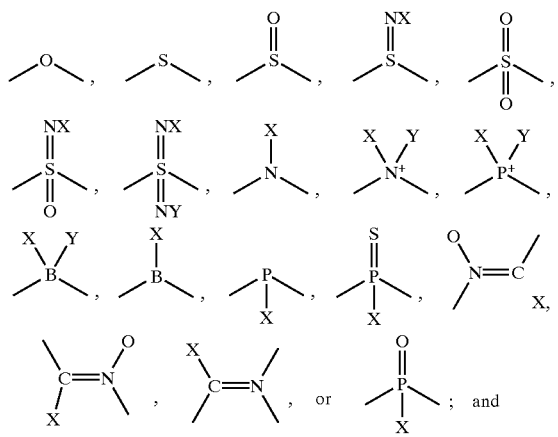

J is of the formula:

\\N=N\\, /O\\N=N/, \\N=N\\O/, \\N=C=N\\

\\C=C=C/Y\\X, or —C≡C— wherein:
A) each X and Y is independently a group of the formula:

—(L)$_m$—Z;

and
B) m is an integer from 0 to 8; and
C) no more than two E groups are adjacent to each other and no J groups are adjacent to each other;

iii) each Z is independently selected from:
A) hydrogen, halo, cyano, nitro, nitroso, azido, chlorate, bromate, iodate, isocyanato, isocyanido, isothiocyanato, pentafluorothio, or
B) a group G, wherein G is an unsubstituted or substituted; unsaturated, partially saturated, or saturated; monocyclic, bicyclic, tricyclic, or fused; carbocyclic or heterocyclic ring system wherein;
1) when the ring system contains a 3 or 4 membered heterocyclic ring, the heterocyclic ring contains 1 heteroatom;
2) when the ring system contains a 5, or more, membered heterocyclic ring or a polycyclic heterocyclic ring, the heterocyclic or polycyclic heterocyclic ring contains from 1 to 4 heteroatoms;
3) each heteroatom is independently selected from N, O, and S;
4) the number of substituents is from 0 to 5 and each substituent is independently selected from X;

2) the total number of non-hydrogen atoms in each compound is 50 or less; and
its enantiomers, stereoisomers, salts, and mixtures thereof;
b) a packaging material.

For the purposes of this invention, in the structural representations of the various L groups each open bond indicates a bond to another L group, a Z group, or the cyclopropene moiety. For example, the structural representation

/O\\ indicates an oxygen atom with bonds to two other atoms; it does not represent a dimethyl ether moiety.

Another embodiment of this invention is a method to inhibit an ethylene response in a plant comprising the step of enclosing the plant in packaging which incorporates the composition of this invention.

A further embodiment is a method to prolong the life of a plant comprising the step of enclosing the plant in packaging which incorporates the composition of this invention.

Another embodiment of this invention is a method to deliver a cyclopropene compound to a plant to inhibit an ethylene response in the plant comprising the step of enclosing the plant in the composition of this invention.

As used herein, the term "halo" means fluorine, chlorine, bromine, and iodine.

Preferably, the number of non-hydrogen atoms in each compound is less than 25. More preferably, the number of non-hydrogen atoms in each compound is less than 20. Even more preferably, the number of non-hydrogen atoms in each compound is less than 13. Most preferably, the number of non-hydrogen atoms in the compound is less than 7.

Preferably, two of $R^1$, $R^2$, $R^3$, and $R^4$ are hydrogen. More preferably, $R^1$ and $R^2$ are hydrogen or $R^3$ and $R^4$ are hydrogen. Even more preferably, $R^2$, $R^3$, and $R^4$ are hydrogen or $R^1$, $R^2$, and $R^4$ are hydrogen. Most preferably, $R^2$, $R^3$, and $R^4$ are hydrogen.

Preferably, $R^1$ is ($C_1$–$C_{10}$) alkyl and $R^2$, $R^3$, and $R^4$ are hydrogen. More preferably, $R^1$ is ($C_1$–$C_8$) alkyl and $R^2$, $R^3$, and $R^4$ are hydrogen. Even more preferably $R^1$ is ($C_1$–$C_4$) alkyl and $R^2$, $R^3$, and $R^4$ are hydrogen. Most preferably, $R^1$ is methyl and $R^2$, $R^3$, and $R^4$ are hydrogen.

Typical $R^1$, $R^2$, $R^3$, and $R^4$ groups include, for example: alkenyl, alkyl, alkynyl, acetylaminoalkenyl, acetylaminoalkyl, acetylaminoalkynyl, alkenoxy, alkoxy, alkynoxy, alkoxyalkoxyalkyl, alkoxyalkenyl, alkoxyalkyl, alkoxyalkynyl, alkoxycarbonylalkenyl, alkoxycarbonylalkyl, alkoxycarbonylalkynyl, alkylcarbonyl, alkylcarbonyloxyalkyl, alkyl(alkoxyimino) alkyl, carboxyalkenyl, carboxyalkyl, carboxyalkynyl, dialkylamino, haloalkoxyalkenyl, haloalkoxyalkyl, haloalkoxyalkynyl, haloalkenyl, haloalkyl, haloalkynyl, hydroxyalkenyl, hydroxyalkyl, hydroxyalkynyl, trialkylsilylalkenyl, trialkylsilylalkyl, trialkylsilylalkynyl, dialkylphosphonato, dialkylphosphato, dialkylthiophosphato, dialkylaminoalkyl, alkylsulfonylalkyl, alkylthlioalkenyl, alkylthioalkyl, alkylthioalkynyl, dialkylaminosulfonyl, haloalkylthioalkenyl, haloalkylthioalkyl, haloalkylthioalkynyl, alkoxycarbonyloxy; cycloalkenyl, cycloalkyl, cycloalkynyl, acetylaminocycloalkenyl, acetylaminocycloalkyl, acetylaminocycloalkynyl, cycloalkenoxy, cycloalkoxy, cycloalkynoxy, alkoxyalkoxycycloalkyl, alkoxycycloalkenyl, alkoxycycloalkyl, alkoxycycloalkynyl, alkoxycarbonylcycloalkenyl, alkoxycarbonylcycloalkyl, alkoxycarbonylcycloalkynyl, cycloalkylcarbonyl, alkylcarbonyloxycycloalkyl, carboxycycloalkenyl, carboxycycloalkyl, carboxycycloalkynyl, dicycloalkylamino, halocycloalkoxycycloalkenyl, halocycloalkoxycycloalkyl, halocycloalkoxycycloalkynyl, halocycloalkenyl, halocycloalkyl, halocycloalkynyl, hydroxycycloalkenyl, hydroxycycloalkyl, hydroxycycloalkynyl, trialkylsilylcycloalkenyl, trialkylsilylcycloalkyl, trialkylsilylcycloalkynyl, dialkylaminocycloalkyl, alkylsulfonylcycloalkyl, cycloalkylcarbonyloxyalkyl, cycloalkylsulfonylalkyl, alkylthiocycloalkenyl, alkylthiocycloalkyl, alkylthiocycloalkynyl, dicycloalkylaminosulfonyl, haloalkylthiocycloalkenyl, haloalkylthiocycloalkyl, haloalkylthiocycloalkynyl; aryl, alkenylaryl, alkylaryl, alkynylaryl, acetylaminoaryl, aryloxy, alkoxyalkoxyaryl, alkoxyaryl, alkoxycarbonylaryl, arylcarbonyl, alkylcarbonyloxyaryl, carboxyaryl, diarylamino, haloalkoxyaryl, haloaryl, hydroxyaryl, trialkylsilylaryl, dialkylaminoaryl, alkylsulfonylaryl, arylsulfonylalkyl, alkylthioaryl, arylthioalkyl, diarylaminosulfonyl, haloalkylthioaryl; heteroaryl, alkenylheteroaryl, alkylheteroaryl, alkynylheteroaryl, acetylaminoheteroaryl, heteroaryloxy, alkoxyalkoxyheteroaryl, alkoxyheteroaryl, alkoxycarbonylheteroaryl, heteroarylcarbonyl, alkylcarbonyloxyheteroaryl, carboxyheteroaryl, diheteroarylamino, haloalkoxyheteroaryl, haloheteroaryl, hydroxyheteroaryl, trialkylsilylheteroaryl, dialkylaminoheteroaryl, alkylsulfonylheteroaryl, heteroarylsulfonylalkyl, alkylthioheteroaryl, heteroarylthioalkyl, diheteroarylaminosulfonyl, haloalkylthioheteroaryl; heterocyclyl, alkenylheteroycycyl, alkylheteroycycyl, alkynylheteroycycyl, acetylaminoheterocyclyl, heterocyclyloxy, alkoxyalkoxyheterocyclo, alkoxyheterocyclyl, alkoxycarbonylheterocyclyl, heterocyclylcarbonyl, alkylcarbonyloxyheterocyclyl, carboxyheterocyclyl, diheterocyclylamino, haloalkoxyheterocyclyl, haloheterocyclyl, hydroxyheterocyclyl, trialkylsilylheterocyclyl, dialkylaminoheterocyclyl, alkylsulfonylheterocyclyl, alkylthioheterocyclyl, heterocyclylthioalkyl, diheterocyclylaminosulfonyl, haloalkyllthioheterocyclyl; hydrogen, fluoro, chloro, bromo, iodo, cyano, nitro, nitroso, azido, chlorato, bromato, iodato, isocyanato, isocyanido, isothiocyanato, pentafluorothio; acetoxy, carboethoxy, cyanato, nitrato, nitrito, perchlorato, allenyl; butylmercapto, diethylphosphonato, dimethylphenylsilyl, isoquinolyl, mercapto, naphthyl, phenoxy, phenyl, piperidino, pyridyl, quinolyl, triethylsilyl, trimethylsilyl; and substituted analogs thereof.

Typical G groups include, for example: saturated or unsaturated cycloalkyl, bicyclic, tricyclic, polycyclic, saturated or unsaturated heterocyclic, unsubstituted or substituted phenyl, naphthyl, or heteroaryl ring systems such as, for example, cyclopropyl, cyclobutyl, cyclopent-3-en-1-yl, 3-methoxycyclohexan-1-yl, phenyl, 4-chlorophenyl, 4-fluorophenyl, 4-bromophenyl, 3-nitrophenyl, 2-methoxyphenyl, 2-methylphenyl, 3-methyphenyl, 4-methylphenyl, 4-ethylphenyl, 2-methyl-3-methoxyphenyl, 2,4-dibromophenyl, 3,5-difluorophenyl, 3,5-dimethylphenyl, 2,4,6-trichlorophenyl, 4-methoxyphenyl, naphthyl, 2-chloronaphthyl, 2,4-dimethoxyphenyl, 4-(trifluoromethyl)phenyl, 2-iodo-4-methylphenyl, pyridin-2-yl, pyridin-3-yl, pyridin-4-yl, pyrazinyl, pyrimidin-2-yl, pyrimidin-4-yl, pyrimidin-5-yl, pyridazinyl, triazol-1-yl, imidazol-1-yl, thiophen-2-yl, thiophen-3-yl, furan-2-yl, furan-3-yl, pyrrolyl, oxazolyl, isoxazolyl, thiazolyl, isothiazolyl, oxadiazolyl, thiadiazolyl, quinolyl, isoquinolyl, tetrahydrofuryl, pyrrolidinyl, piperidinyl, tetrahydropyranyl, morpholinyl, piperazinyl, dioxolanyl, dioxanyl, indolinyl and 5-methyl-6-chromanyl, adamantyl, norbornyl, and their substituted analogs such as, for example: 3-butyl-pyridin-2-yl, 4-bromo-pyridin-2-yl, 5-carboethoxy-pyridin-2-yl, 6-methoxyethoxy-pyridin-2-yl, The term "packaging material" is used in a generic sense herein to include all components of packaging in which fruits, vegetables, or ornamental plants may be contained such as, for example, packaging films; a container such as, for example, a cardboard, plastic, or wooden box or paper bag; or wax or film coating on the plant or the container. Encapsulated cyclopropenes can be compounded within, or laminated between, different thermoplastic packaging plastics such as polyethylene, ethyl vinylacetate, polyvinyl alcohol or with rigid plastics such as polystyrene, polycarbonate, and polymethyl methacrylate. In addition, the cyclopropene, either free or encapsulated, can be incorporated into various waxes, coated papers, and cardboard or it can be incorporated into an adhesive component of packaging materials or incorporated into package labels.

The amount of cyclopropene to be incorporated into the packaging material will vary depending upon particular cyclopropene, the type and amount of packaging material used, the composition of the packaging material, the quantity of plant material to be enclosed, and the volume to be enclosed. Generally, in order to obtain a concentration of cyclopropene in the enclosed volume of from about 1 part per billion ("ppb") to 1000 parts per million ("ppm") a concentration of the cyclopropene in the packaging material of from 0.0001 to 100 milligrams ("mg") per square meter of surface area of the packaging material is required. Preferably, the concentration of cyclopropene will be from 0.001 to 10 mg per square meter. More preferably from 0.01 to 1 mg per square meter. This corresponds, respectively, to approximately 10 ppb–100 ppm and 100 ppb to 10 ppm of cyclopropene released into the volume packaged by each square meter of packaging material.

The term "enclosing" means to surround, close in, or confine the plant. In the general sense it means to place the plant in close contact with the packaging material so that the plant can be shipped or stored.

Because cyclopropenes are known to release from packaging materials by diffusion or by displacement by water, particularly when the cyclopropene is encapsulated in a molecular encapsulation agent, this invention also contemplates articles in which the composition of this invention is enclosed in a container which is impermeable to the cyclopropene gas, or water, or both. Such an article of manufacture includes, for example, labels in which the cyclopropene is incorporated into the label material itself or the label adhesive.

The cyclopropene can be incorporated directly into many types of packaging materials or it can first be encapsulated into a molecular encapsulation agent which is then subsequently incorporated into packaging materials. Preferred encapsulating agents include cyclodextrins, crown ethers, polyoxyalkylenes, polysiloxanes, and zeolites. More preferred encapsulating agents include α-cyclodextrin, β-cyclodextrin, and γ-cyclodextrin. The most preferred encapsulating agent, particularly when the cyclopropene is 1-methylcyclopropene, is alpha-cyclodextrin. The most preferred encapsulating agent will vary depending upon the size of the R substituents. However, as one skilled in the art will appreciate, any cyclodextrin or mixture of cyclodextrins, cyclodextrin polymers as well as modified cyclodextrins can also be utilized pursuant to the present invention. Cyclodextrins are available from Wacker Biochem Inc., Adrian, Mich. or Cerestar USA, Hammond, Ind., as well as other vendors.

The term "plant" is used in a generic sense herein, and includes woody-stemmed plants such as trees and shrubs. Plants to be packaged as described herein include whole plants and any portions thereof, such as harvested field crops, potted plants, cut flowers (stems and flowers), other ornamental plants, seeds, dormant seedlings, and harvested fruits and vegetables.

The present invention can be employed to modify a variety of different ethylene responses. Ethylene responses may be initiated by either exogenous or endogenous sources of ethylene. Ethylene responses include, for example, the ripening and/or senescence of flowers, fruits and vegetables, abscission of foliage, flowers and fruit, the shortening of life of ornamentals such as potted plants, cut flowers, shrubbery, seeds, and dormant seedlings. Additional ethylene responses or ethylene-type responses that may be inhibited by the composition of the present invention include, for example, auxin activity, inhibition of terminal growth, control of apical dominance, increase in branching, increase in tillering, changing biochemical compositions of plants (such as increasing leaf area relative to stem area), abortion or inhibition of flowering and seed development, stimulation of seed germination and breaking of dormancy, and hormone or epinasty effects.

Methods according to embodiments of the present invention inhibit the ripening and/or senescence of vegetables. As used herein, "vegetable ripening" includes the ripening of the vegetable after having been picked from the vegetable-bearing plant. Vegetables which may be treated by the composition of the present invention to inhibit ripening and/or senescence include leafy green vegetables such as lettuce (e.g., *Lactuea sativa*), spinach (*Spinaca oleracea*), and cabbage (*Brassica oleracea*), various roots, such as potatoes (*Solanum tuberosum*) and carrots (Daucus), bulbs, such as onions (Allium sp.), herbs, such as basil (*Ocimum basilicum*), oregano (*Origanum vulgare*), dill (*Anethum graveolens*), as well as soybean (*Glycine max*), lima beans (*Phaseolus linensis*), peas (Lathyrus spp.), corn (*Zea mays*), broccoli (*Brassica oleracea italica*), cauliflower (*Brassica oleracea botrytis*), and asparagus (*Asparagus officinalis*).

Methods according to embodiments of the present invention inhibit the ripening of fruits. As used herein, "fruit ripening" includes the ripening of fruit after having been picked from the fruit-bearing plant. Fruits which may be treated by the method of the present invention to inhibit ripening include tomatoes (*Lycopersicon esculentum*), apples (*Malus domestica*), bananas (*Musa sapientum*), pears (*Pyrus comrnunis*), papaya (*Carica papaya*), mangoes (*Mangifera indica*), peaches (*Prunus persica*), apricots (*Prunus armeniaca*), nectarines (*Prunus persica nectectarina*), oranges (Citrus sp.), lemons (*Citrus limonia*), limes (*Citrus aurantifolia*), grapefruit (*Citrus paradisi*), tangerines (*Citrus nobilis deliciosa*), kiwi (*Actinidia chinenus*), melons such as cantaloupe (*C. cantalupensis*) and musk melon (*C. melo*), pineapple (*Aranas comosus*), persimmon (Diospyros sp.), various small fruits including berries such as strawberries (Fragaria), blueberries (Vaccinium sp.) and raspberries (e.g., *Rubus ursinus*), green beans (*Phaseolus vulgaris*), members of the genus Cucumis such as cucumber (*C. sativus*), and avocados (*Persea americana*).

Ornamental plants which may be treated by the composition of the present invention to inhibit senescence and/or to prolong flower life and appearance (e.g., delay wilting), include potted ornamentals, and cut flowers. Potted ornamentals and cut flowers which may be treated with the present invention include azalea (Rhododendron spp.), hydrangea (*Macrophylla hydrangea*), hybiscus (*Hibiscus rosasanensis*), snapdragons (Antirrhinum sp.), poinsettia (*Euphorbia pulcherima*), cactus (e.g. *Cactaceae schlumbergera truncata*), begonias (Begonia sp.), roses (Rosa spp.), tulips (Tulipa sp.), daffodils (Narcissus spp.), petunias (*Petunia hybrida*), carnation (*Dianthus caryophyllus*), lily (e.g., Lilium sp.), gladiolus (Gladiolus sp.), alstroemeria (*Alstoemeria brasiliensis*), anemone (e.g., *Anemone blanda*), columbine (Aquilegia sp.), aralia (e.g., *Aralia chinensis*), aster (e.g., *Aster carolinianus*), bougainvillea (Bougainvillea sp.), camellia (Camellia sp.), bellflower (Campanula sp.), cockscomb (celosia sp.), falsecypress (Chamaecyparis sp.), chrysanthemum (Chrysanthemum sp.), clematis (Clematis sp.), cyclamen (Cyclamen sp.), freesia (e.g., *Freesia refracta*), and orchids of the family Orchidaceae.

Plants which may be treated by the method of the present invention to inhibit abscission of foliage, flowers and fruit include cotton (Gossypium spp.), apples, pears, cherries (*Prunus avium*), pecans (*Carva illinoensis*), grapes (*Vitis vinifera*), olives (e.g. *Vitis vinifera* and *Olea europaea*), coffee (*Coffea arabica*), snapbeans (*Phaseolus vulgaris*), and weeping fig (*ficus benjamina*), as well as dormant seedlings such as various fruit trees including apple, ornamental plants, shrubbery, and tree seedlings. In addition, shrubbery which may be treated according to the present invention to inhibit abscission of foliage include privet (Ligustrum sp.), photinea (Photinia sp.), holly (Ilex sp.), ferns of the family Polypodiaceae, schefflera (Schefflera sp.), aglaonema (Aglaonema sp.), cotoneaster (Cotoneaster sp.), barberry (Berberis sp.), waxmyrtle (Myrica sp.), abelia (Abelia sp.), acacia (Acacia sp.) and bromeliades of the family Bromeliaceae.

As used herein, all percentages are percent by weight and all parts are parts by weight, unless otherwise specified, and are inclusive and combinable. All ratios are by weight and all ratio ranges are inclusive and combinable. All molar ranges are inclusive and combinable.

Many of the cyclopropenes applicable to this invention are known materials prepared using the processes disclosed in U.S. Pat. Nos. 5,518,988 and 6,017,849. The cyclopropene/molecular encapsulation agent complexes of the present invention are prepared by contacting the cyclopropene with a solution or slurry of the molecular encapsulation agent and then isolating the complex, again using general processes disclosed in U.S. Pat. No. 6,017,849. In the case of 1-methylcyclopropene, the gas is bubbled through a solution of α-cyclodextrin in water from which the complex first precipitates and is then isolated by filtration.

The compounds of this invention can be prepared by a number of methods. For general references see Closs, G. L. *Advan. Alicyclic Chem.* 1966, 1, 53–127 and Al Dulayymi, A. R.; Al Dulayymi, J. R; Baird, M. S.; and Koza, G. *Russian Journal of Organic Chemistry* 1997, 33, 798–816.

The reaction of a bromo-olefin with dibromocarbene gives a tribromocyclopropane, which can be converted to the cyclopropene with methyllithium or other organolithium compounds as shown. (see Baird, M. S.; Hussain, H. H.; Nethercott, W *J. Chem. Soc. Perkin Trans.* 1, 1986, 1845–1854 and Baird, M. S.; Fitton, H. L.; Clegg, W; McCamley, A. *J. Chem. Soc. Perkin Trans.* 1, 1993, 321–326). If one equivalent of methyllithium or other alkyllithium is used, the mono-brominated cyclopropene is obtained. With 2 or more equivalents of the alkyllithium, the lithiated cyclopropene is formed. This can be quenched with water to give the cyclopropenes shown (E=H). Alternatively, the cyclopropenyllithium can be reacted with electrophiles to give derivatived cyclopropenes. Examples of such electrophiles include alkylating agents, trisubstituted chlorosilanes, borates, dialkyl or diaryl disulfides, ketones, aldehydes, esters, amides and nitrites.

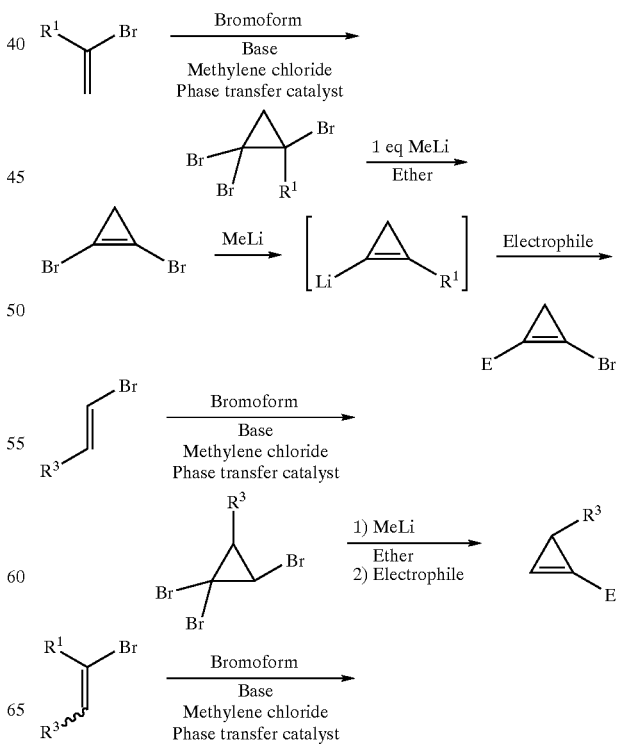

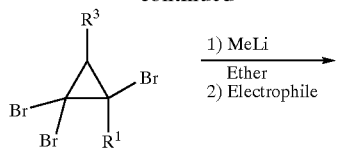

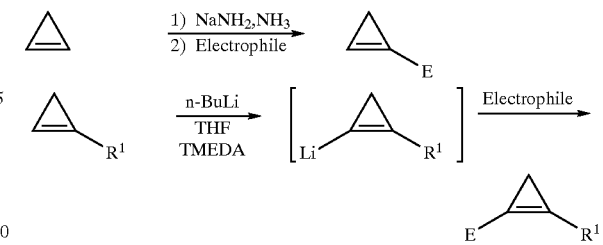

The bromo-olefins can be prepared by standard methods. Chloro-olefins can be used in place of bromo-olefins.

The tribrominated cyclopropanes can also be converted to mono-brominated cyclopropanes with reducing agents such as diethylphosphite. Other reducing agents could be used.

Tribromocyclopropanes or cyclopropenes containing an alcohol can be converted to a good leaving group such as a sulfonate derivative. The leaving group can be displaced with nucleophiles to give other substituted cyclopropenes.

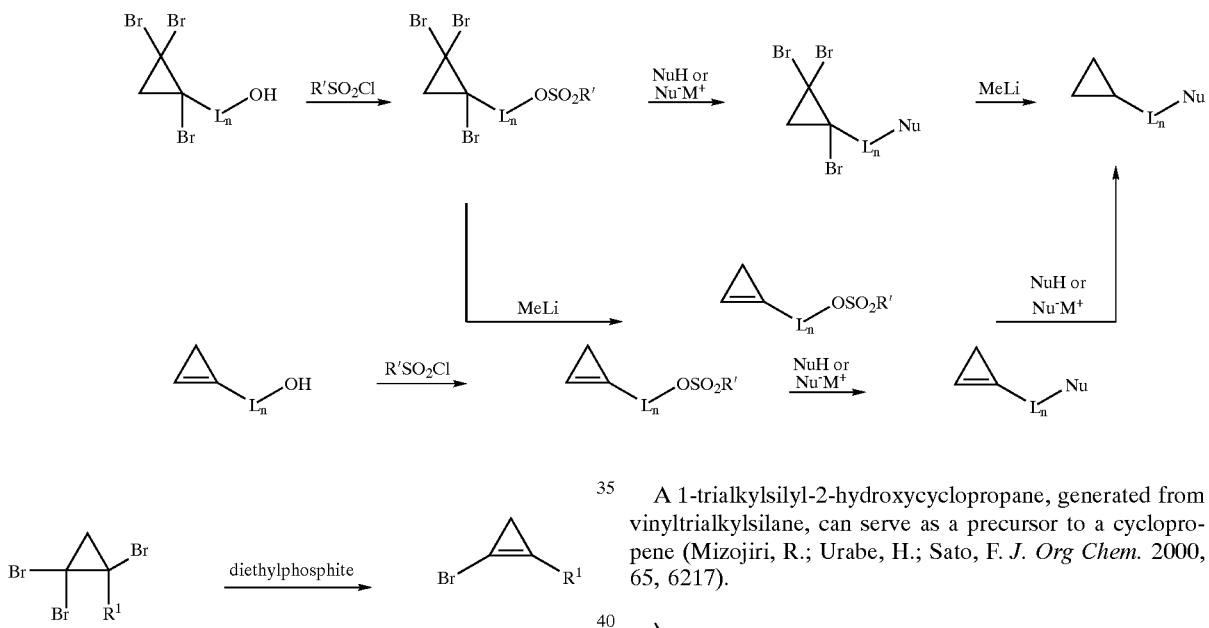

A 1,1-disubstituted olefin can also react with dibromocarbene to give a dibrominated intermediate. This can be reduced with zinc to the mono-brominated cyclopropane. Elimination of the bromide with base gives the cyclopropene (reference Binger, P. *Synthesis* 1974, 190).

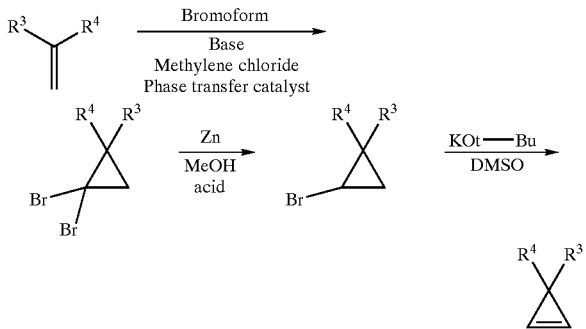

Cyclopropene can be deprotonated with a strong base such as sodium amide in liquid ammonia and reacted with an alkyl halide or other electrophiles to give a substituted cyclopropene (reference: Schipperijn, A. J.; Smael, P.,; *Recl. Trav. Chin. Pays-Bas,* 1973, 92, 1159). Substituted cyclopropenes can be deprotonated with alkyllithium reagents and reacted with electrophiles.

A 1-trialkylsilyl-2-hydroxycyclopropane, generated from vinyltrialkylsilane, can serve as a precursor to a cyclopropene (Mizojiri, R.; Urabe, H.; Sato, F. *J. Org Chem.* 2000, 65, 6217).

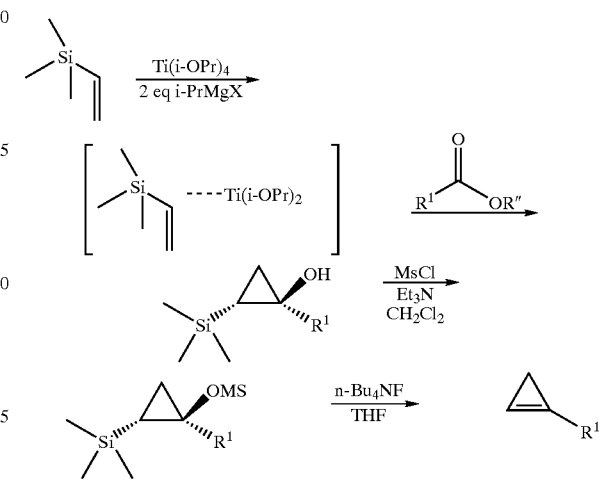

1-Trialkylsilyl-2-halocyclopropanes also undergo a fluoride catalyzed elimination to give cyclopropenes (Billups, W. E.; Lee, G-A; Arney, B. E.; Whitmire, K. H. *J. Am. Chem. Soc.,* 1991, 113, 7980. and Banwell, M. G.; Corbett, M.; Gulbis, J.; Mackay, M. F.; Reum, M. E. *J. Chem. Soc. Perkin Trans.* 1, 1993, 945).

The addition of a diazo compound to an acetylene is another method that can be used for the synthesis of cyclo propenes (Mueller, P.; Cranisher, C; *Helv. Chim. Acta* 1993, 76, 521).

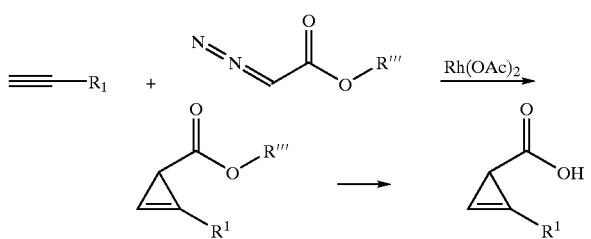

The esters can be hydrolyzed to the carboxylic acid.

Similarly, dihalocarbenes can be added to acetylenes to give 1-alkyl-3,3-dihalocyclopropenes (Bessard, Y.; Schlosser, M.; *Tetrahedron,* 1991, 47, 7323).

Compounds of this invention can also be obtained from a malonate derivative as shown.

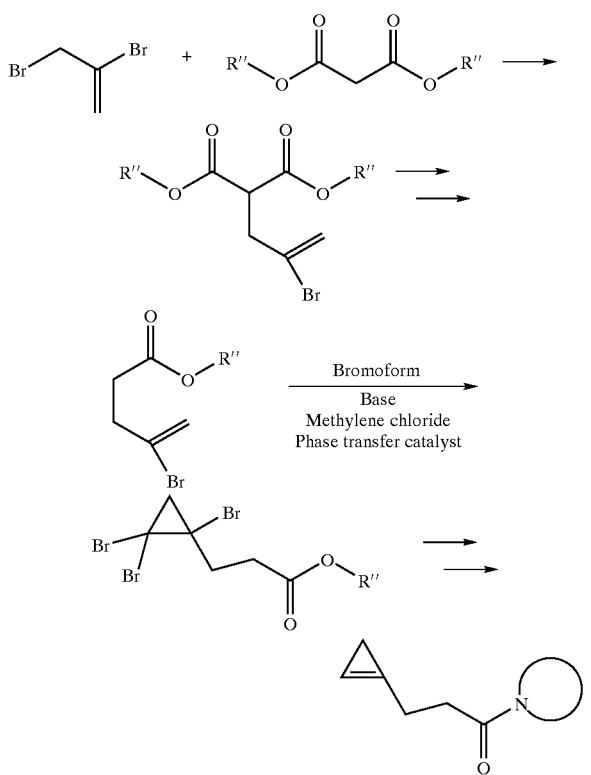

Other methods for making cyclopropenes can be found in the following references: Duerr, H.,*Angew. Chem.* 1967, 24, 1104; Closs et al., *J. Am. Chem.* 1963, 85, 3796; Baird, M. S.; Dale, C. M.; Al Dulayymi, J. R. *J. Chem. Soc. Perkin Trains.* 1, 1993, 1373–1374; Koster, R. et al., *Liebigs Annalen Chem.* 1973, 1219–1235; Closs, G. L.; Closs, L. E., *J. Am. Chem. Soc.,* 1961, 83, 1003–1004; Stoll, A. T.; Negishi, E., *Tetrahedron Lett.* 1985, 26, 5671–5674.

EXAMPLES

General: All cyclopropenes were stored at −80° C. All reactions were carried out under an atmosphere of nitrogen. Flash chromatography of cyclopropenes was carried out under an atmosphere of nitrogen. All target compounds were 80% or greater purity unless otherwise noted. 1-Substitued cyclopropenes are never heated, and care should be taken to minimize the amount of time that these compounds are at room temperature.

Example 1

Preparation of 1-Chloro-4-cycloprop-1-enylmethyl-benzene (Compound 1)

a. 1-(2-Bromo-allyl)-4-chloro-benzene

A solution of 8 ml (0.0622 mol) of 2,3-dibromopropene in 50 ml diethyl ether was placed under a nitrogen atmosphere by use of a Firestone valve. While cooling in an ice water bath, a solution of 62 ml (0.062 mol) of 1M 4-chlorophenylmagnesium bromide in diethyl ether was added slowly via addition funnel. After stirring for 2 hours while warming to room temperature, the reaction was recooled in an ice bath and 50 ml of 1 N hydrochloric acid was then added via syringe. The resulting mixture was transferred to a separatory funnel and the phases were separated. The organic layer was dried over $MgSO_4$ and filtered. The solvent was removed from the filtrate in vacuo. The residue was triturated with cold pentanes to yield 12.0 g of 1-(2-bromo-allyl)-4-chloro-benzene as an oil which was used in without further purification.

b. 2-(4-Chlorophenylmethyl)-1,1,2-tribromocyclopropane

To a solution of 11.4 g (0.0494 mol) of 1-(2-bromo-allyl)-4-chloro-benzene in 20 ml of bromoform was added 0.686 g (0.00213 mol) tetrabutylammonium bromide. After heating to 58.5° C. for an hour, 10.7 ml (0.0494 mol) of 50% aqueous sodium hydroxide was added. This was repeated seven times over two days. After cooling to room temperature there was added hexanes and water. This mixture was gravity filtered through qualitative fluted filter paper. The resulting mixture was transferred to a separatory funnel and the phases were separated. The organic layer was dried over $MgSO_4$ and filtered. The solvent was removed from the filtrate in vacuo. This residue was purified by column chromatography with hexanes to give 2.3 g of 2-(4-chlorophenylmethyl)-1,1,2-tribromocyclopropane.

c. 1-(4-Chlorophenylmethyl)-cyclopropene

A solution of 1.20 g (0.00298 mol) of 2-(4-chlorophenylmethyl)-1,1,2-tribromocyclopropane in 6 ml of diethyl ether was placed under a nitrogen atmosphere via use of a Firestone valve. While cooling in an ice water bath, 6.38 ml (0.00893 mol) of 1.4M methyl lithium in diethyl ether was added slowly by syringe. After 15 minutes, 2 ml of water was added via syringe. The resulting mixture was transferred to a separatory funnel and the phases were separated. The organic layer was dried over $MgSO_4$ and filtered. The solvent was removed from the filtrate in vacuo with a bath temperature under 20° C. to yield 0.430 g of 1-(4-chlorophenylmethyl)-cyclopropene as an oil.

Example 2

Preparation of 1-(2-Thienyl)methyl-cyclopropene (Compound 2)

The Grignard reagent of 2-bromothiophene was prepared, and converted to 1-(2-thienyl)methyl-cyclopropene by the same reaction sequence as was used for the preparation of compound 1.

Example 3

Preoaration of 2-(3-Cycloprop-1-enyl-propyl)-[1,3]dioxane (Compound 3)

The Grignard reagent of 2-(2-bromoethyl)-1,3-dioxane was prepared, and converted to 2-(3-cycloprop-1-enyl-propyl)-[1,3]dioxane by the same reaction sequence as was used for the preparation of compound 1.

Example 4

Preparation of 1-(6-(Phenyldimethylsilyl)-hexyl)-cyclopropene (Compound 4)

a. 2-Bromo-8-(phenyldimethylsilyl)-oct-1-ene

Commercially available pentamethylenebis(magnesium bromide) (37 ml, 0.5 M in THF, 18.5 mmol) was cooled in an ice bath. A solution of 3.16 g (18.5 mmol) of phenyldimethylchlorosilane in roughly 7 ml of THF was added. The reaction mixture was stirred at 5° C. for 15 minutes then at room temperature for 35 minutes, then recooled to 5° C. 2,3-Dibromopropene (3.7 g, 18.5 mmol) in roughly 5 ml of THF was added to the reaction mixture, which was held at 5° C. for 5 minutes, then warmed to room temperature and stirred overnight. The reaction mixture was quenched with water. Ether and a small amount of 1N HCl was added. The phases were separated, and the organic phase was washed with water and brine, dried over magnesium chloride and stripped. Column chromatography gave 1.47 g of 2-bromo-8-(phenyldimethylsilyl)-oct-1-ene as a colorless oil.

b. N,N'-dibenzyl-N,N,N',N'-tetramethylethylenediammonium Dibromide and N,N'-dibenzyl-N,N,N',N'-tetraethylethylenediammonium Dibromide (Phase Transfer Catalysts)

To a stirred solution of 16.5 g (142 mmol) of N,N,N',N'-tetramethylethylenediamine in 60 g of acetonitrile was added 50.1 g (292 mmol) of benzyl bromide. The mixture self warmed and was allowed to stir for 2.5 hours whereon a heavy precipitate was observed. The slurry was diluted with diethyl ether, filtered, washed with diethyl ether and dried yielding 61.8 g of the desired N,N'-dibenzyl-N,N,N',N'-tetramethylethylenediammonium dibromide, a white solid mp 230–232° C.

In an analogous way, using N,N,N',N'-tetraethylethylenediamine one obtains N,N'-dibenzyl-N,N,N',N'-tetraethylethylenediammonium dibromide, a white solid mp 190–193° C., decomposes.

c. 2-(6-(Phenyldimethylsilyl)-hexyl)-1,1,2-tribromocyclopropane

A mixture of 1.4 g (4.3 mmol) of 2-bromo-8-(phenyldimethylsilyl)-oct-1-ene, 3.2 g of 45% aqueous potassium hydroxide solution (25.6 mmol), 0.2 g N,N'-dibenzyl-N,N,N',N'-tetraethylethylenediammonium dibromide, and 7.5 ml of methylene chloride was treated with 1.1 ml of bromoform (12.6 mmol). The well-stirred reaction mixture was held overnight at room temperature. Water and methylene chloride were added, the phases were separated. The methylene chloride phase was dried over magnesium sulfate, and stripped. A small amount of heptane was added during the strip to help remove remaining bromoform. Column chromatography gave 1.02 g of 2-(6-(phenyldimethylsilyl)-hexyl)-1,1,2-tribromocyclopropane as a colorless liquid.

d. 1-(6-(Phenyldimethylsilyl)-hexyl)-cyclopropene

A solution of 0.95 g (1.9 mmol) of 2-(6-(phenyldimethylsilyl)-hexyl)-1,1,2-tribromocyclopropane in ether was cooled to −78° C. Excess methyllithium (1.4M, 4.1 ml, 5.7 mmol) was added, and the reaction mixture was placed in an ice bath for 30 min, then quenched with water. The phases were separated. The ether phase was washed with water, washed with brine, dried over magnesium sulfate and stripped to give 200 mg of 1-(6-(phenyldimethylsilyl)-hexyl)-cyclopropene as a colorless liquid.

Example 5

Preparation of 1-($\alpha,\alpha$-dimethylbenzyl)-cyclopropene (Compound 5)

a. $\alpha,\alpha$-dimethylbenzylcyanide

Into a 1000 ml 3 necked flask with mechanical stirring, an external water bath, an internal thermometer, a condenser and an addition funnel was added 250 g of dimethyl sulfoxide, 59 g (504 mmol) of benzyl cyanide, and 160 g (1127 mmol) of methyl iodide. The internal temperature was raised to +45° C. and then 83 g of 50% aqueous NaOH was added at 0.7 drops per second. After two hours the addition was complete. The thick slurry was cooled, diluted with 1000 ml of water and 500 ml of diethyl ether and 500 ml of hexane. The organic layer was separated and concentrated. It contained mono and dimethylated compounds. To this concentrate was further added 250 g of dimethyl sulfoxide, 60 g of methyl iodide, and 37 g of 50% aqueous NaOH for two hours as above. After cooling, dilution with 1000 ml of water, 500 ml of diethyl ether, and 500 ml of hexane gave an organic layer which was washed with 500 ml of water, dried over anhydrous magnesium sulfate and evaporated in vacuo yielding 69 g of $\alpha,\alpha$-dimethylbenzylcyanide.

b. $\alpha,\alpha$-Dimethylbenzyl Methyl Ketone

Into a 500 ml round bottomed flask with magnetic stirring, a reflux condenser and a septum under an atmosphere of dry nitrogen was added 30 g (207 mmol) of $\alpha,\alpha$-dimethylbenzylcyanide and 200 ml of diethyl ether. Methyllithium (1.4 M, 160 ml, 224 mmol) in diethyl ether was added via cannula over three minutes. The reaction exothermed to a mild reflux during the addition. After stirring for 20 minutes, the reaction was quenched by the slow addition of 45 ml of concentrated aqueous hydrochloric acid diluted with 100 ml of water. After stirring for one hour, the organic layer was separated, dried over anhydrous magnesium sulfate, and evaporated in vacuo yielding 32 g of $\alpha,\alpha$-dimethylbenzyl methyl ketone.

c. 1-($\alpha,\alpha$-Dimethylbenzyl)-1-chloroethylene

Into a 250 ml round bottomed flask equipped with magnetic stirring and a reflux condenser was placed 15 g (98 mmol) of $POCl_3$, 30 g (145 mmol) of $PCl_5$, and 19.9 g (123 mmol) of $\alpha,\alpha$-dimethylbenzyl methyl ketone. The reaction was heated in an oil bath to an external temperature of 110° C. Gas evolution ceased after one hour. The reaction was cooled and carefully poured onto ice and aqueous ammonium hydroxide. Extractive workup with diethyl ether gave a mixture of 1-($\alpha,\alpha$-dimethylbenzyl)-1-chloroethylene and 1-($\alpha,\alpha$-dimethylbenzyl)-1,1-dichloroethane. Vacuum distillation gave purified 1-($\alpha,\alpha$-dimethylbenzyl)-1-chloroethylene bp (23 torr) 110–120° C.

d. 1-($\alpha,\alpha$-Dimethylbenzyl)-1-chloro-2,2-dibromocyclopropane

Into a 100 ml round bottomed flask equipped with magnetic stirring was added 4.5 g (25 mmol) of 1-($\alpha,\alpha$-dimethylbenzyl)-1-chloroethylene, 25 g (100 mmol) of bromoform, 27 g of methylene chloride, 0.37 g of N,N'-dibenzyl-N,N,N'N'-tetramethylethylenediammonium dibromide, and 12.4 g (100 mmol) of 45% aqueous KOH. Rapid stirring overnight gave a 20% conversion to the desired cyclopropane. Washing the aqueous layer with water and resubmitting with fresh bromoform, catalyst, and KOH overnight gave further conversion. A third submission was deemed adequate. The aqueous washed organic layer was evaporated in vacuo and chromatographed on silica gel using 2% diethyl ether in hexane yielding 4.2 g of 1-($\alpha,\alpha$-dimethylbenzyl)-1-chloro-2,2-dibromocyclopropane.

e. 1-($\alpha,\alpha$-Dimethylbenzyl)-cyclopropene

Into a 50 ml flask equipped with a stirbar and septum and under an atmosphere of dry nitrogen was added 1.73 g (4.9 mmol) of 1-($\alpha,\alpha$-dimethylbenzyl)-1-chloro-2,2-dibromocyclopropane and 12 ml of diethyl ether. After cooling in an ice bath for 10 minutes, 9.0 ml (12.6 mmol) of 1.4 M methyllithium in diethyl ether was added via syringe. A precipitate formed immediately. After stirring for 10 minutes the reaction was quenched with 3 ml of water. The aqueous layer was removed and the organic layer was dried over anhydrous magnesium sulfate and evaporated in vacuo with the bath temperature at +25° C. yielding 0.94 g of 1-($\alpha,\alpha$-dimethylbenzyl)-cyclopropene.

Example 6

Preparation of 3-Methyl-3-phenylcyclopropene (Compound 6)

a. 2,2-Dibromo-1-methyl-1-phenylcyclopropane

To a solution of 12.5 ml (0.0963 mol) of α-methylstyrene in 30.4 ml (0.348 mol) of bromoform and 1.34 g (0.00416 mol) of tetrabutylammonium bromide was added slowly via addition funnel 20.9 ml (0.400 mol) of 50% aqueous sodium hydroxide. After heating to 55° C. for 1 hour 20.9 ml (0.400 mol) of 50% aqueous sodium hydroxide was added. After 2 additional hours of heating, the reaction was cooled to room temperature when hexanes and water were added. The resulting mixture was transferred to a separatory funnel and the phases were separated. The organic layer was dried over $MgSO_4$ and filtered. The solvent was removed from the filtrate in vacuo. The product was isolated by vacuum distillation to yield 24.1 g of 2,2-dibromo-1-methyl-1-phenylcyclopropane as an oil.

b. 2-Bromo-1-methyl-1-phenylcyclopropane

To a solution of 6.40 g (0.0221 mol) of 2,2-dibromo-1-methyl-1-phenylcyclopropane in 22 g of methanol was added 2.16 g (0.0360 mol) glacial acetic acid and 2.11 g (0.0323 mol) of zinc dust. After stirring at room temperature for 4 hours, the solvent was removed it vacuo. To the resulting residue hexanes and water were added. The resulting mixture was transferred to a separatory funnel and the phases were separated. The organic layer was dried over $MgSO_4$ and filtered. The solvent was removed from the filtrate in vacuo to yield 3.24 g of 2-bromo-1-methyl-1-phenylcyclopropane as an oil which was used without further purification.

c. 3-Methyl-3-phenylcyclopropene

To a solution of 1.56 g (0.00739 mol) of 2-bromo-1-methyl-1-phenylcyclopropane in 5 ml of dimethylsulfoxide was added 1.429 g (0.0127 mol) of potassium tert-butoxide. After the reaction was heated to 72° C. for 4 hours, diethyl ether and water were added. The resulting mixture was transferred to a separatory funnel and the phases were separated. The organic layer was dried over $MgSO_4$ and filtered. The solvent was removed from the filtrate in vacuo to yield 0.88 g of 70% pure 3-methyl-3-phenylcyclopropene as an oil. The major byproduct (roughly 20%) was 1-methyl-1-phenylcyclopropane.

Example 7

Preparation of 3-Methyl-3-Phenoxymethylcycloprop-2-ene (Compound 7)

Methallyl phenyl ether was converted to 3-methyl-3-phenoxymethylcycloprop-2-ene with 90% purity in a similar manner to the conversion of (x-methylstyrene to 3-methyl-3-phenylcyclopropene (Example 6).

Example 8

Preparation of 1-methyl-2-benzylcyclopropene (Compound 8)

Into a 50 ml flask equipped with a stirbar and septum and under an atmosphere of dry nitrogen was added 1 mg of 1,10-phenanthroline, 1.34 g (11.5 mmol) of N,N,N',N'-tetramethylethylenediamine, and 25 ml of tetrahydrofuran. The mixture was cooled to −30° C. and 1.5 ml (22 mmol) of 1-methylcyclopropene (prepared from 3-chloro-2-methylpropene; see Hopf, H.; Wachholz, G.; Walsh, R. *Chem. Ber.* 1985, 118, 3579, and Köster, R et al., *Liebigs Annalen Chem.* 1973, 1219–1235) was added via syringe. Addition of 1.0 ml of 1.6 M butyllithium in hexanes was needed to produce a dark rust colored solution. Further addition of 6.0 ml of the 1.6 M butyllithium solution (9.6 mmol) and stirring for 15 minutes at −30° C. gave a solution of the lithiated 1-methylcyclopropene. Addition of 1.64 g of benzyl bromide and slow warming over 20 minutes to +5° C. gave lightened color. The reaction was quenched with 0.5 ml of methanol, rapidly evaporated in vacuo with a bath temperature of +25° C., partitioned between diethyl ether and dilute aqueous hydrochloric acid, dried with anhydrous magnesium sulfate and re-evaporated in vacuo yielding 1.3 g of 1-methyl-2-benzylcyclopropene.

Example 9

1-(2-(4-Chlorophenylthio)ethyl)cyclopropene (Compound 9)

a. 2-Bromo-4-(1-ethoxy-ethoxy)-but-1-ene

While cooling a solution of 10.38 g (0.0687 mol) of 3-bromo-3-buten-1-ol in 20 ml of diethyl ether with 50 mg (0.000263 mol) p-toluene sulfonic acid monohydrate in an ice water bath, 19 ml (0.199 mol) of ethyl vinyl ether was added slowly dropwise to maintain an internal temperature of <10° C. After 1 hour at 0° C., a few drops of triethylamine was added. The reaction mixture was poured onto water. The resulting mixture was transferred to a separatory funnel and the phases were separated. The isolated organic layer was washed with brine then dried over potassium carbonate and filtered. The solvent was removed from the filtrate in vacuo to yield 14.04 g of 2-bromo-4-(1-ethoxy-ethoxy)-but-1-ene as an oil.

b. 1,1,2-Tribromo-2-[2-(1-ethoxy-ethoxy)-ethyl]-cyclopropane

To a solution of 14.02 g (0.0628 mol) 2-bromo-4-(1-ethoxy-ethoxy)-but-1-ene in 108 ml methylene chloride with 0.5–0.9 ml 45% aqueous potassium hydroxide was added 16.4 ml (0.118 mol) of bromoform and 2.88 g (0.00628 mol) of N,N'-dibenzyl-N,N,N',N'-tetramethylethylenediammonium dibromide and 28 ml (0.314 mol) 45% aqueous potassium hydroxide. After 3 days the reaction mixture was poured onto water. The resulting mixture was transferred to a separatory funnel and the phases were separated. To the isolated organic layer was added 2.88 g (0.00628 mol) of N,N'-dibenzyl-N,N,N',N'-tetramethylethylenediammonium dibromide and 28 ml (0.314 mol) 45% aqueous potassium hydroxide. After 24 hours, hexanes and water were added. This mixture was gravity filtered through qualitative fluted filter paper. The resulting mixture was transferred to a separatory funnel and the phases were separated. The organic layer was dried over $MgSO_4$ and filtered. The solvent was removed from the filtrate in vacuo to yield 17.0 g of 1,1,2-tribromo-2-[2-(1-ethoxy-ethoxy)-ethyl]-cyclopropane as an oil.

c. 1,1,2-Tribromo-2-(2-hydroxyethyl)cyclopropane

To a slurry of 16.5 g (0.0418 mol) of 1,1,2-tribromo-2-[2-(1-ethoxy-ethoxy)-ethyl]-cyclopropane in 145 ml methanol and 40 ml water, was added 0.306 g (0.00161 mol) p-toluene sulfonic acid monohydrate and 145 ml 6M hydrochloric acid. After stirring at room temperature for 1 hour, the solvent was removed from the reaction mixture in vacuo. To the residue, there was added ethyl acetate and water. The resulting mixture was transferred to a separatory funnel and the phases were separated. The isolated organic layer was washed with brine then dried over $MgSO_4$ and filtered. The solvent was removed from the filtrate in vacuo to yield 11.9 g of 1,1,2-tribromo-2-(2-hydroxyethyl)cyclopropane as an oil.

d. 1,1,2-Tribromo-2-(2-benzenesulfonyloxyethyl) cyclopropane

While cooling a solution of 3.00 g (0.00929 mol) of 1,1,2-tribromo-2-(2-hydroxyethyl)cyclopropane in methylene chloride with 0.901 ml (0.0111 mol) pyridine to 0° C., 1.18 ml (0.00929 mol) of benzene sulfonyl chloride was added dropwise via pipet. Allowed to warm to room temperature. After 3 days, water was added. The resulting mixture was transferred to a separatory funnel and the phases were separated. The organic layer was dried over $MgSO_4$ and filtered. The solvent was removed from the filtrate in vacuo to yield 3.10 g of 80% pure 1,1,2-tribromo-2-(2-benzenesulfonyloxyethyl)cyclopropane as an oil.

e. 2-(2-(4-Chlorophenylthio)ethyl)-1,1,2-tribromocyclopropane

To a solution of 0.234 g (0.162 mol) of 4-chlorothiophenol in 3 ml methanol was added 0.371 ml (0.00162 mol) of 25% sodium methoxide in methanol. After stirring at room temperature for about 1 hour, the solvent was removed in vacuo. A solution of 0.750 g (0.00151 mol) of 1,1,2-tribromo-2-(2-benzenesulfonyloxyethyl)-cyclopropane in anhydrous N,N-dimethylformamide was added to the residue. After stirring at room temperature for 24 hours, the reaction mixture was poured onto water and extracted with ethyl acetate. The organic layer was dried over $MgSO_4$ and filtered. The solvent was removed from the filtrate in vacuo to yield 0.750 g of an oil which was subsequently purified by column chromatography with 0.5% to 1% diethyl ether/hexanes to yield 0.500 g of 2-(2-(4-chlorophenyl-thio)ethyl)-1,1,2-tribromocyclopropane as an oil.

f. 1-(2-(4-Chlorophenylthio)ethyl)cyclopropene

A solution of 0.500 g (0.0011 mol) of 2-(2-(4-chlorophenylthio)ethyl)-1,1,2-tribromocyclopropane in 6 ml of diethyl ether was placed under a nitrogen atmosphere by use of a Firestone valve. While cooling in an ice water bath, 2.38 ml (0.00334 mol) of 1.4 M methyl lithium in diethyl ether was added slowly via syringe. After 15 minutes, 2 ml of water was added via syringe. The resulting mixture was transferred to a separatory funnel and the phases were separated. The organic layer was dried over $MgSO_4$ and filtered. The solvent was removed from the filtrate in vacuo with a bath temperature under 20° C. to yield 0.100 g of 1-(2-($^4$-chlorophenylthio)ethyl)cyclopropene as an oil.

Example 10

2-(2-Benzenesulfonyloxyethyl)-cyclopropene (Compound 10)

A solution of 0.745 g (0.00150 mol) of 1,1,2-tribromo-2-(2-benzenesulfonyloxyethyl)-cyclopropane in 4 ml of diethyl ether was placed under a nitrogen atmosphere by use of a Firestone valve. While cooling to −78° C. in a dry ice/acetone bath, 23.45 ml (0.00450 mol) of 1.4 M methyl lithium in diethyl ether was added slowly via syringe. After 15 minutes warmed to 0° C. in an ice water bath then returned to −78° C. for about 30 minutes before 2 ml of water was added via syringe. The resulting mixture was transferred to a separatory funnel and the phases were separated. The organic layer was dried over $MgSO_4$ and filtered. The solvent was removed from the filtrate in vacuo with a bath temperature under 20° C. to yield >0.155 g of 70% pure 2-(2-benzenesulfonyloxyethyl)-cyclopropene contaminated with 30% 1-(2-hydroxyethyl)cyclopropene as an oil.

Example 11

Preparation of 2-(1-(4-Bromopyrazole))-1-ethylcyclopropene (Compound 11)

a. 2-Hydroxy-1-ethylcyclopropene

A solution of 1.15 g (3.6 mmol) of 1,1,2-tribromo-2-(2-hydroxyethyl)cyclopropane, (preparation described above) in 40 ml of ether was cooled to −78° C. Methyllithium (1.4M, 10.3 ml, 14.4 mmol) was added. The reaction mixture was warmed to 5° C. and held for one half hour. The reaction was quenched with water and the phases were separated. The ether phase was washed with water, washed with brine, dried over magnesium sulfate and stripped. The crude product was immediately used in the next reaction.

b. 2-Methanesulfonyl-1-ethylcyclopropene

The crude product of the above reaction was dissolved in 5 ml of ether and cooled in an ice bath. Triethylamine (1 ml) was added, then 0.49 g of methanesulfonyl chloride (4.3 mmol) was added. The reaction mixture was stirred for 1 hour. Water and additional ether were added and the phases were separated. The ether phase was washed with water twice, washed with brine, dried over magnesium sulfate and stripped to give 380 mg of 2-methanesulfonyl-1-ethylcyclopropene as a pale yellow liquid.

c. 2-(1-(4-Bromopyrazole))-1-ethylcyclopropene

To a suspension of 60% sodium hydride (0.13 g, 3.3 mmol) in 5 ml of DMF is added 0.51 g of 4-bromopyrazole (3.5 mmol). The reaction was stirred for 15 minutes at room temperature, then cooled in an ice bath. 2-Methanesulfonyl-1-ethylcyclopropene (280 mg, 1.7 mmol) was added. The ice bath was removed, and the reaction was stirred at room temperature for 2 hours. Ether and water were added to the reaction mixture and the phases were separated. The aqueous phase was extracted with additional ether. The combined ether phases were washed with water three times, washed with brine, dried over magnesium sulfate and stripped. The product was chromatographed to give 30 mg of 72% pure 2-(1-(4-bromopyrazole))-1-ethylcyclopropene.

Example 12

Preparation of 7-(1-Imidazole)-1-heptylcyclopropene (Compound 12)

a. 1-(1-Ethoxyethoxy)-6-bromohexane

To a cooled solution of 80 mg of toluenesulfonic acid in 40 ml of ether was fed 20 g (110 mmol) of 6-bromohexanol and 40 ml of ethyl vinyl ether simultaneously by separate additional funnels. The temperature of the reaction mixture was kept at 7° C. or lower during the feeds, which took 1 hour. The reaction mixture was stirred 20 minutes longer, then roughly 1 ml of triethylamine was added. The reaction mixture was washed with water and brine, dried over potassium carbonate, filtered and stripped to give 25.7 g of a pale yellow liquid, which was used without further purification.

b. 9-(1-Ethoxyethoxy)-2-bromonon-1-ene

A slurry of 5.6 g of magnesium turnings (230 mmol) in 100 ml of THF was treated with a small amount of 1,2-dibromoethane. 1-(1-Ethoxyethoxy)-6-bromohexane (38.5 g, 152 mmol) was fed slowly to the reaction mixture, maintaining the temperature at 40–50° C. At the end of the addition the reaction mixture was held 20 minutes, then transferred by cannula to solution of 33.4 g (167 mmol) of 2,3-dibromopropene in 25 ml of THF at 0° C. The reaction mixture was stirred at 0° C. for 15 minutes, then stirred at room temperature for 15 minutes, then quenched with water. The reaction mixture was transferred into a separatory funnel. A small amount of 1 N HCl was added, the phases were separated, the ether phase was washed with water and brine, then dried over magnesium sulfate, filtered, and stripped to give 33.63 g of a yellow liquid which was used without further purification.

c. 1,1,2-Tribromo-2-(7-hydroxyheptyl)cyclopropane

A mixture of 9-(1-ethoxyethoxy)-2-bromonon-1-ene (33.63 g, 115 mmol), 4.1 g of N,N'-dibenzyl-N,N,N',N'-tetraethylethylenediammonium dibromide, 42 g of 45% potassium hydroxide (337 mmol), 93 g of bromoform (368 mmol) and 280 g of methylene chloride were rapidly stirred at room temperature for two days. When the reaction stalled, the reaction mixture was transferred to a separatory funnel and washed with water. The methylene chloride phase was transferred to a flask and treated with the same amount of the phase transfer catalyst and 45% potassium hydroxide as above, then stirred at room temperature for an additional 3 days. The reaction mixture was washed with water, the methylene chloride phase was dried with magnesium sulfate, and then stripped. The product was treated with 320 ml of methanol and 40 ml of 1N HCl for 1 hour at room temperature. The methanol was stripped, ethyl acetate was added. The organic phase was washed with water and brine, then treated with 200 ml of silica gel. Filtration followed by a strip gave 38 g of black product. This was chromatographed on silica gel to give 19.0 g of 1,1,2-tribromo-2-(7-hydroxyheptyl)cyclopropane as a pale yellow liquid.

d. 1-(7-Hydroxyheptyl)-cyclopropene

A solution of 1.0 g 1,1,2-tribromo-2-(7-hydroxyheptyl) cyclopropane (2.5 mmol) in 25 ml of ether was treated at −78° C. with 7.2 ml of methyllithium (1.4 M, 10 mmol). After 5 minutes, the reaction mixture was warmed to 0° C. and held at this temperature. The reaction was quenched with saturated ammonium chloride. The reaction mixture was washed with water and brine, dried over magnesium sulfate, filtered and stripped to give 240 mg of 1-(7-hydroxyheptyl)-cyclopropene.

e. 1-(7-Methanesulfonyloxyheptyl)-cyclopropene

A solution of 3.8 mmol of 1-(7-hydroxyheptyl)-cyclopropene in 50 ml of ether was cooled in an ice bath. Triethylamine (1 ml) and 0.48 g of methanesulfonyl chloride (4.2 mmol) were added and the reaction mixture was stirred for 2½ hours at 0° C. The reaction mixture was washed with water and brine, dried over magnesium sulfate, filtered and stripped to give 1-(7-methanesulfonyloxyheptyl)-cyclopropene which was used without further purification.

f. 7-(1-Imidazole)-1-heptylcyclopropene

To a suspension of 60% sodium hydride (0.08 g, 2 mmol) in 5 ml of DMF in an ice bath is added 0.14 g of imidazole (2 mmol). The reaction was stirred for 15 minutes, then 0.3 g (1.3 mmol) of 1-(7-methanesulfonyloxyheptyl)-cyclopropene in 3 ml of DMF was added. The reaction mixture was stirred for 10 minutes, then the ice bath was removed, and the reaction was stirred at room temperature for 1 hour. Ether and water were added to the reaction mixture and the phases were separated. The aqueous phase was extracted with additional ether. The combined ether phases were washed with water three times, washed with brine, dried over magnesium sulfate and stripped. The product was chromatographed to give 80 mg of 7-(1-imidazole)-1-heptylcyclopropene.

Example 13

Preparation of 7-(diphenylamino)-1-heptylcyclopropene (Compound 13)

Diphenylamine (0.42 g, 2.5 mmol) in 10 ml of THF was cooled to −78° C. and treated with 1.6 ml (1.4M, 2.2 mmol) methyllithium. 1-(7-Methanesulfonyloxyheptyl)-cyclopropene was added, the bath was removed, and the reaction mixture was allowed to warm to room temperature. The reaction was held for 5.5 hours, then quenched with water. Ether and water were added to the reaction mixture and the phases were separated. The ether phase was washed with water twice, washed with brine, dried over magnesium sulfate and stripped. The product was chromatographed to give 80 mg of 7-(diphenylamino)-1-heptylcyclopropene as a colorless liquid.

Example 14

Preparation of 1-cyclohexylcyclopropene (Compound 14)

1-Cyclohexyl-2-(trimethylsilyl)cyclopropanol was prepared from methyl cyclohexylcarboxylate and vinyltrimethylsilane as described in Mizojiri, R.; Urabe, H.; Sato, F. *J. Org Chem.* 2000, 65, 6217. This material was converted to the cyclopropene in an analogous manner to that described in the same reference.

Example 15

Preparation of 1-((2-Carboxy-N-morpholino)ethyl)-cyclopropene a. 2-(2-Bromo-allyl)-malonic Acid Diethyl Ester The oil was removed from 21.70 g (0.542 mol) of 60% sodium hydride in oil by washing with hexanes. To the residue suspended in 200 ml tetrahydrofuran, 84.38 ml (0.556 mol) diethyl malonate was added slowly via addition funnel. While the reaction was cooled to −35 to −10° C., 100 g (0.400 mol) of 2,3-dibromopropene was added slowly via addition funnel. After heating to reflux for 1 hour, the reaction was cooled to room temperature and concentrated ill vacuo. Hexanes and water were added to the residue and the resulting mixture was transferred to a separatory funnel where the phases were separated. The isolated organic layer was washed with IN hydrochloric acid then dried over magnesium sulfate and filtered. The solvent was removed from the filtrate in vacuo to yield 154 g of 2-(2-bromo-allyl)-malonic acid diethyl ester as an oil.

b. 2-(2-Bromo-allyl)-malonic Acid

A mixture of 10.5 g (0.0376 mol) of 2-(2-bromo-allyl)-malonic acid diethyl ester and 37.6 ml (0.470 mol) of 50% aqueous sodium hydroxide was stirred at room temperature for 4 days. The reaction mixture was extracted with diethyl ether. The isolated aqueous layer was acidified by the addition of concentrated hydrochloric acid and diethyl ether was added. The resulting mixture was transferred to a separatory funnel where the phases were separated. The isolated organic layer dried over magnesium sulfate and filtered. The solvent was removed from the filtrate in vacuo to yield 5.3 g of 2-(2-bromo-allyl)-malonic acid as a solid which was carried on without purification.

c. 4-Bromo-pent-4-enoic Acid 5.3 g (0.0238 mol) of neat, unpurified 2-(2-bromo-allyl)-malonic acid was heated to 125–130° C. for 8 hours to yield 3.73 g of 4-bromo-pent-4-enoic acid which was carried on without purification.

d. 4-Bromo-pent-4-enoic Acid Ethyl Ester

To a solution of 3.73 g (0.0208 mol) of unpurified 4-bromo-pent-4-enoic acid in 3 ml chloroform with 1 drop of N,N-dimethylformamide was added 1.18 ml (0.0162 mol) of thionyl chloride. After this mixture had been heated to 60° C. for 30 minutes, it was added to a solution of 2.46 ml (0.0436 mol) ethanol and 1.97 ml (0.024 mol) pyridine and 13 ml methylene chloride. After stirring for 30 minutes, the reaction mixture was concentrated in vacuo. To the residue was added diethyl ether and water. The resulting mixture was transferred to a separatory funnel where the phases were separated. The isolated organic layer was dried over magnesium sulfate and filtered. The solvent was removed from the filtrate in vacuo to yield 3.5 g of 4-bromo-pent-4-enoic acid ethyl ester as an oil which was purified via vacuum distillation.

e. 1,1,2-Tribromo-2-((3-carboethoxy)ethyl)-cyclopropane 1,1,2-Tribromo-2-((3-carboethoxy)ethyl-cyclopropane was prepared in a manner similar to that described for the corresponding intermediate in Example 9.

The residue obtained was purified by column chromatography with diethyl ether/hexanes.

f. 1,1,2-Tribromo-2-((2-carboxy)ethyl)-cyclopropane

After a solution of 10.2 g (0.0269 mol) of 1,1,2-tribromo-2-((3-carboethoxy)-ethyl)cyclopropane in 40 ml (0.736 mol) of 48% hydrobromic acid and 40 ml of water was heated to reflux for 8 hours, it was cooled to room temperature and then vacuum filtered through Shark Skin® filter paper. The isolated solid was washed with water before adding diethyl ether. The solution was transferred to a separatory funnel where it was washed with saturated aqueous sodium bicarbonate which was isolated and made acidic by the addition of 1N hydrochloric acid. The aqueous solution was returned to a separatory funnel and extracted with diethyl ether. The isolated organic layer was dried over magnesium sulfate and filtered. The solvent was removed from the filtrate in vacuo to yield 5.9 g of 1,1,2-tribromo-2-((2-carboxy))-ethylcyclopropane as a solid which was used as is.

g. 1,1,2-Tribromo-2-((2-carboxy-N-morpholino)ethyl)-cyclopropane

To a slurry of 0.97 g (0.00276 mol) of 1,1,2-tribromo-2-((2-carboxy))-ethyl-cyclopropane in 2 ml of chloroform were added 1 drop of N,N-dimethylformamide and 0.434 ml (0.00596 mol) of thionyl chloride. After 15 minutes of heating to reflux, the reaction mixture was concentrated in vacuo. A solution of this residue in 2 ml of methylene chloride was added to a solution of 0.486 ml (0.00552 mol) of morpholine in 1 ml of methylene chloride being cooled to −20° C. After 30 minutes the reaction mixture was concentrated in vacuo. The resulting residue was extracted from a minimal amount of IN hydrochloric acid with ethyl acetate. The organic layer was dried over $MgSO_4$ and filtered. The solvent was removed from the filtrate in vacuo to yield 1.08 g of 1,1,2-mo-2-((2-carboxy-N-morpholino)ethyl)-cyclopropane as an oil.

h. 1-((2-Carboxy-N-morpholino)ethyl)-cyclopropene 0.460 g of 60% pure 1-((2-carboxy-N-morpholino)ethyl)-cyclopropene was red in a manner similar to compound 1.

In a similar manner the following compounds were made:

TABLE 1

Additional compounds

| Cmpd # | $R^1$ | $R^2$ | $R^3$ | $R^4$ | Purity % | Comments |
|---|---|---|---|---|---|---|
| 16 | H | H | 4-Methoxy-phenoxy-methyl | $CH_3$ | 30 | 30% 1-(4-methoxyphenoxymethyl)-1-methylcyclopropane |
| 17 | benzyl | H | H | H | | |
| 18 | phenethyl | H | H | H | | |
| 19 | H | H | phenethyl | $CH_3$ | 55 | 36% 1-phenethyl-1-methylcyclopropane |
| 20 | H | H | benzyl | $CH_3$ | 50 | 24% 1-benzyl-1-methylcyclopropane |
| 21 | 2-cyclohexylethyl | H | H | H | | |
| 22 | cycloheptylmethyl | H | H | H | | |
| 23 | cyclohexylmethyl | H | H | H | | |
| 24 | 4-methylbenzyl | H | H | H | | |
| 25 | 3-phenylpropyl | H | H | H | | |
| 26 | 2-methoxybenzyl | H | H | H | | |
| 27 | 4-phenylbutyl | H | H | H | | |
| 28 | 2-(4-chloro-phenyl)ethyl | H | H | H | 72 | |
| 29 | 3-methylbenzyl | H | H | H | | |
| 30 | 2,4,6-trimethyl-benzyl | H | H | H | 40 | 49% 3-(2,4,6-trimethylphenyl)-2-bromopropene |
| 31 | cyclopentyl-methyl | H | H | H | | |
| 32 | 7-(1-pyrazole)-heptyl | H | H | H | | |
| 33 | 3-(2-(1,3-dioxolane))-propyl | H | H | H | 75 | 10% of the tribromocyclopropane precursor |
| 34 | 7-(1-(1,2,4-triazole))-heptyl | H | H | H | | |
| 35 | 2-(2-pyridylthio)-ethyl | H | H | H | | |

The compounds were characterized using a variety of spectroscopic techniques. The NMR data for compounds 1–35 is given in Table 2. For compounds containing impurities, the chemical shifts of the impurities are not reported, and the integrals are adjusted to reflect only the contribution of the target compound.

TABLE 2

NMR Data

| cmpd # | NMR |
|---|---|
| 1 | (CDCl3): 1.0(d,2H), 3.8(s,2H), 6.6(m,1H), 7.2(d,2H), 7.25 (d,2H) |
| 2 | (CDCl3): 1.0(d,2H), 4.0(s,2H), 6.6(m,1H), 6.95(d,1H), 7.0 (m,1H), 7.2(d,1H) |
| 3 | (CDCl3): 0.88(d,2H), 1.3(d,2H), 1.5–1.8(m,2H), 2.0–2.2(m, 2H), 2.5(m,2H), 3.7–3.9(m,2H), 4.1–4.2(m,2H), 4.55(m,1H), 6.5(m,1H) |
| 4 | (CDCl3): 0.25(s,6H), 0.7–0.8(m,2H), 0.87(d,2H), 1.2–1.4(m, 6H), 1.5–1.7(m,2H), 2.45(t,2H), 6.45(bs,1H), 7.3–7.45(m,3H), 7.45–7.6(m,2H) |

TABLE 2-continued

NMR Data

| cmpd # | NMR |
|---|---|
| 5 | (CDCl3): 1.05(s,2H), 1.53(s,6H), 6.5(s,1H), 7.1–7.5(m,5H). |
| 6 | (d6 Acetone): 1.6(s,3H), 7.1–7.3(m,5H), 7.45(s,2H) |
| 7 | (CDCl3): 1.3(s,3H), 3.9(s,2H), 6.8–7.0(m,3H), 7.25(m,2H), 7.35(s,2H) |
| 8 | (CDCl3): 0.89(2H,s), 2.03(3H,s), 3.75(2H,s), 7.1–7.4(5H,m) |
| 9 | (CDCl3): 0.94(d,2H), 2.8(t,2H), 3.1(t,2H), 6.6(m,1H), 7.3 (m,4H) |
| 10 | (CDCl3): 0.85(d,2H), 2.8(t,2H), 4.3(t,2H), 6.6(m,1H), 7.6 (m,2H), 7.7(m,1H), 7.9(m,2H) |
| 11 | (CDCl3): 0.92(d,2H), 1.58(s,4H), 3.05(t,2H), 4.55(t,2H), 6.6 (bs,1H), 7.39(s,1H), 7.47(s,1H) |
| 12 | (CDCl3): 0.87(d,2H), 1.2–1.4(m,6H), 1.57(m,2H), 1.79 (m,2H), 2.47(td,2H), 3.92(t,2H), 6.44(m,1H), 6.90(bs,1H), 7.06 (bs,1H), 7.46(bs,1H) |
| 13 | (CDCl3): 0.87(d,2H), 1.2–1.4(m,6H), 1.5–1.8(m,4H), 2.47 (t,2H), 3.67(t,2H), 6.42(bs,1H), 6.9–7.1(m,6H), 7.2–7.4(m,4H) |
| 14 | (CDCl3): 0.88(d,2H), 1.2–1.5(m,5H), 1.55–2.0(m,5H), 2.4–2.6 (m,2H), 6.40(t,1H) |
| 15 | (CDCl3): 0.90(d,2H), 2.6–2.9(m,4H), 3.6–3.8(m,8H), 6.5 (m,1H) |
| 16 | (CDCl3): 1.2(s,3H), 3.8(s,3H), 3.9(s,2H), 6.8(m,4H), 7.35 (s,2H) |
| 17 | (CDCl3): 1.1(d,2H), 3.8(s,2H), 6.5(m,1H), 7.2–7.35(m,5H) |
| 18 | (CDCl3): 0.92(d,2H), 2.8(t,2H), 2.9(t,2H), 6.45(m,1H), 7.15–7.3(m,5H) |
| 19 | (CDCl3): 1.18(s,3H), 1.78(m,2H), 2.42(m,2H), 7.1–7.2(m,3H), 7.2–7.3(m,2H), 7.3(s,2H) |
| 20 | (CDCl3): 1.17(s,3H), 2.76(s,2H), 7.1(m,2H), 7.15–7.3(m,3H), 7.35(s,2H) |
| 21 | (CDCl3): 0.89(d,2H), 0.88–1.0,(m,1H), 1.1–1.35(m,4H), 1.47 (q,2H), 1.6–1.85(m,4H), 2.48(td,2H), 6.42(t,1H) |
| 22 | (CDCl3): 0.87(d,2H), 1.15–1.3,(m,2H), 1.35–1.9(m,11H), 2.40 (dd,2H), 6.43(t,1H) |
| 23 | (CDCl3): 0.87(d,2H), 0.9–1.05,(m,2H), 1.1–1.35(m,3H), 1.4–1.8(m,6H), 2.37(dd,2H), 6.40(t,1H) |
| 24 | (CDCl3): 1.0(d,2H), 2.3(s,3H), 3.8(s,2H), 6.56(m,1H), 7.1 (m,4H) |
| 25 | (CDCl3): 0.9(d,2H), 1.9(m,2H), 2.45(t,2H), 2.6(t,2H), 6.5 (m,1H), 7.1–7.3(m,5H) |
| 26 | (CDCl3): 1.0(d,2H), 3.8(s,3H), 6.55(m,1H), 6.9(m,2H), 7.2 (m,2H) |
| 27 | (CDCl3): 0.88(d,2H), 1.6–1.75(m,4H), 2.55(t,2H), 2.65(t,2H), 6.4(m,1H), 7.15(m,3H), 7.25(m,2H) |
| 28 | (CDCl3): 0.9(d,2H), 2.7–2.8(m,2H), 2.8–2.9(m,2H), 6.5 (m,1H), 7.15(d,2H), 7.3(d,2H) |
| 29 | (CDCl3): 1.0(d,2H), 2.3(s,3H), 3.8(s,2H), 6.58(m,1H), 7.1 (m,3H), 7.2(m,1H) |
| 30 | (CDCl3): 0.9(d,2H), 2.25(m,9H), 3.75(s,2H), 6.45(m,1H), 6.85(s,1H) |
| 31 | (CDCl3): 0.89(d,2H), 1.1–1.3(m,2H), 1.45–1.65(m,4H), 1.65–1.85(m,2H), 2.15(m,1H), 2.45(d,2H), 6.44(m,1H) |
| 32 | (CDCl3): 0.87(d,2H), 1.2–1.4(m,6H), 1.56(pentet,2H), 1.87 (pentet,2H), 2.46(td,2H), 4.12(t,2H), 6.23(t,1H), 6.42(t,1H), 7.36(d,1H), 7.50(d,1H) |
| 33 | (CDCl3): 0.89(d,2H), 1.7(m,4H), 2.5(m,2H), 3.8–4.0(m,4H), 4.9(m,1H), 6.47(m,1H) |
| 34 | (CDCl3): 0.87(d,2H), 1.2–1.4(m,6H), 1.57(m,2H), 1.88 (m,2H), 2.47(t,2H), 4.17(t,2H), 6.43(bs,1H), 7.94(s,1H), 8.04(s,1H) |
| 35 | (CDCl3): 0.97(d,2H), 2.9(t,2H), 3.4(t,2H), 6.6(m,1H), 6.98 (m,1), 7.16(m,1H), 7.49m,1H), 8.4(m,1H) |

It is often desirable to include in the composition one or more adjuvants, such as extenders, binders, lubricants, surfactants and/or dispersants, wetting agents, spreading agents, dispersing agents, stickers, adhesives, defoamers, thickeners, emulsifying agents and the like. Such adjuvants commonly used in the art can be found in the John W. McCutcheon, Inc. publication *Detergents and Emulsifiers, Annual*, Allured Publishing Company, Ridgewood, N.J., U.S.A.

Another embodiment of this invention is a method to deliver a cyclopropene compound to a plant to inhibit an ethylene response in the plant comprising the step of contacting the composition of this invention with water in the presence of the plant.

Some embodiments of this invention are illustrated by the following examples:

Example 16

1-MCP Release from Polyvinyl Alcohol (PVA) Film Containing 1-MCP/α-cyclodextrin Complex 1-MCP/α-cyclodextrin complex powder (0.05 grams) was heat sealed into a 2×3.5 inch piece of 1.5 mil thick M 7061 polyvinyl alcohol (PVA) film (Chris Craft Corp.) using a Sealmaster 420 (Audion Elektro) heat sealer. This film was placed into a 36 liter volume high humidity chamber. Care was taken to ensure that the film did not directly contact any water. The 1-MCP release characteristics of the film versus time were determined by periodically analyzing the atmosphere in the chamber for 1-MCP. The analysis method was gas chromatography using a flame ionization detector. Table 3 shows the 1-MCP concentration in the chamber versus time. The results clearly show that 1-MCP was released from the PVA film just by the water provided by humidity.

TABLE 3

| Time in Humid Chamber | Concentration of 1-MCP (ppm) |
|---|---|
| 0 min. | 0.0 |
| 5 min. | 0.9 |
| 25 min. | 2.2 |
| 45 min. | 3.2 |
| 90 min. | 6.0 |
| 20 hr. | 17.0 |

Example 17

1-MCP Release from Low Density Polyethylene (LDPE) Film Containing 1-MCP/α-Cyclodextrin Complex 1-MCP/α-CD complex powder (0.05 grams) was heat sealed into a 5.5×12 inch piece of 2.0 mil thick low density polyethylene (LDPE) film. This film was placed into a 36 liter volume high humidity chamber. Care was taken to ensure that the film did not directly contact any water. The 1-MCP release characteristics of the film versus time were determined by periodically analyzing the atmosphere in the chamber for 1-MCP. The analysis method was gas chromatography using a flame ionization detector. Table 4 shows the 1-MCP concentration in the chamber versus time. The results clearly show that 1-MCP was released from the LDPE film just by the water provided by humidity.

TABLE 4

| Time in Humid Chamber | Concentration of 1-MCP (ppm) |
|---|---|
| 0 min. | 0.0 |
| 5 min. | 2.0 |
| 20 min. | 7.7 |
| 40 min. | 14.5 |
| 60 min. | 19.0 |

Example 18

1-MCP Release from Waxy, Cast Film Containing 1-MCP/α-Cyclodextrin Complex

Parafilm® "M" film (2.0 grams, American National Can Corp.) was dissolved/dispersed in 12 grams of hexane.

1-MCP/α-cyclodextrin complex powder (0.5 grams) was mixed into this suspension and then the whole mixture was poured into a 3.5 inch diameter glass crystallizing dish to dry. The dish was placed in a 50° C. oven for 5 hrs. to dry and the resulting cast film was removed from the dish. This film was placed into a 36 liter volume high humidity chamber being careful not to allow the film to contact any water directly. The 1-MCP release characteristics of the film versus time were determined by periodically analyzing the atmosphere in the chamber for 1-MCP. The analysis method was gas chromatography using a flame ionization detector. Table 5 shows the 1-MCP concentration in the headspace versus time. The results clearly show that 1-MCP was released from the LDPE film just by the water provided by humidity.

TABLE 5

| Time in Humid Chamber | Concentration of 1-MCP (ppm) |
|---|---|
| 0 min. | 0.0 |
| 5 min. | 0.02 |
| 20 min. | 0.1 |
| 35 min. | 0.3 |
| 60 min. | 0.8 |
| 90 min. | 1.4 |

Example 19

1-MCP Release from High Density Polyethylene (HDPE) Film

High density polyethylene (HDPE) film of 2 mil thickness measuring 4.5×2.75 inches was exposed to 2206 ppm 1-MCP (vol/vol) in the atmosphere of a sealed quart jar for 2 hours. The film was removed, allowed to stand in air for 5 minutes and then sealed in a fresh quart jar equipped with a sampling septum. The 1-MCP release characteristics of the film versus time were determined by periodically analyzing the atmosphere in the jar for 1-MCP. The analysis method was gas chromatography using a flame ionization detector. Table 6 shows the results, which indicate significant release of 1-MCP from the film.

TABLE 6

| Time in Jar | Concentration of 1-MCP (ppm) |
|---|---|
| 0 sec. | 0.0 |
| 0.5 min. | 3.0 |
| 5 min. | 8.0 |
| 15 min. | 9.6 |
| 60 min. | 11.0 |

Example 20

1-MCP Release from Wax Paper

Wax paper measuring 4.5×2.75 inches was exposed to 2206 ppm 1-MCP (vol/vol) in the atmosphere of a sealed quart jar for 5 hours. The film was removed, allowed to stand in air for 5 minutes and then sealed in a fresh quart jar equipped with a sampling septum. The 1-MCP release characteristics of the film versus time were determined by periodically analyzing the atmosphere in the jar for 1-MCP. The analysis method was gas chromatography using a flame ionization detector. Table 7 shows the results, which indicate less release than Example 4, but still a significant amount of 1-MCP.

TABLE 7

| Time in Jar | Concentration of 1-MCP (ppm) |
|---|---|
| 0 min. | 0.0 |
| 0.5 min. | 0.3 |
| 5 min. | 0.9 |
| 15 min. | 0.9 |
| 60 min. | 0.9 |

I claim:
1. A composition comprising:
a) a compound of the formula:

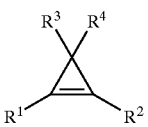

wherein:
1) each $R^1$, $R^2$, $R^3$, and $R^4$ is independently a group of the formula:

—(L)$_n$—Z wherein:
i) n is an integer from 0 to 12;
ii) each L is independently selected from a member of the group D, E, or J wherein:
D is of the formula:

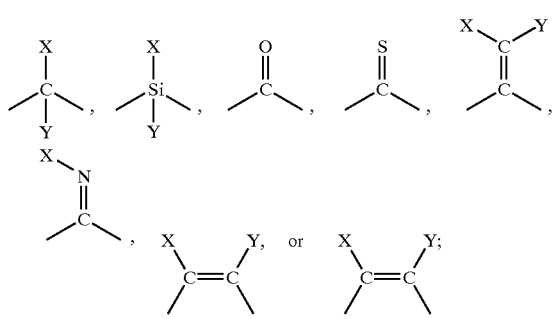

E is of the formula:

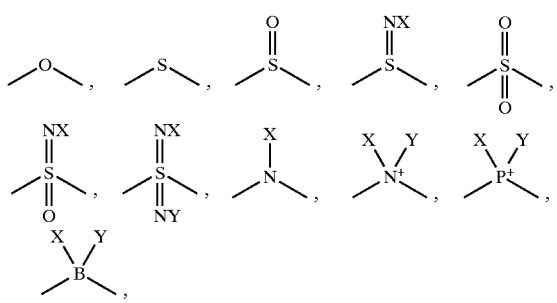

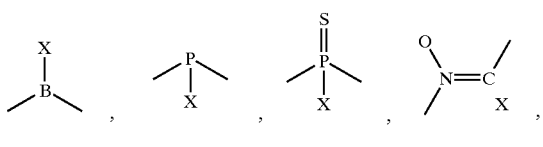

-continued $$\diagdown C=N\diagup^O_X, \quad \diagdown_{N=C}\diagup^X_{\diagdown}, \quad \diagdown_{C=N}\diagup^X_{\diagup}, \text{ or }$$

$$\diagdown\underset{X}{\overset{O}{\underset{\|}{P}}}\diagdown_X \text{; and}$$

J is of the formula:

$$\diagdown_{N=N}\diagdown, \quad \diagup_{N=N}\diagdown^O, \quad \diagdown_{N=N}\diagup^O,$$

$$\diagdown_{N=C=N}\diagdown, \quad \underset{X}{\diagdown}{C=C=C}\diagup^Y_{\diagdown}, \text{ or }$$

—C≡C— wherein:
A) each X and Y is independently a group of the formula:

—(L)$_m$—Z;

and
B) m is an integer from 0 to 8; and
C) no more than two E groups are adjacent to each other and no J groups are adjacent to each other;

iii) each Z is independently selected from:
A) hydrogen, halo, cyano, nitro, nitroso, azido, chlorate, bromate, iodate, isocyanato, isocyanido, isothiocyanato, pentafluorothio, or
B) a group G, wherein G is an unsubstituted or substituted; unsaturated, partially saturated, or saturated; monocyclic, bicyclic, tricyclic, or fused; carbocyclic or heterocyclic ring system wherein;
1) when the ring system contains a 3 or 4 membered heterocyclic ring, the heterocyclic ring contains 1 heteroatom;
2) when the ring system contains a 5, or more, membered heterocyclic ring or a polycyclic heterocyclic ring, the heterocyclic or polycyclic heterocyclic ring contains from 1 to 4 heteroatoms;
3) each heteroatom is independently selected from N, O, and S;
4) the number of substituents is from 0 to 5 and each substituent is independently selected from X;

2) the total number of non-hydrogen atoms in each compound is 50 or less; and its enantiomers, stereoisomers, salts, and mixtures thereof; and b) a packaging material.

2. The composition of claim 1, wherein $R^1$ is ($C_1$–$C_{10}$) alkyl and $R^2$, $R^3$, and $R^4$ are hydrogen.

3. The composition of claim 1, wherein $R^1$ is ($C_1$–$C_4$) alkyl and $R^2$, $R^3$, and $R^4$ are hydrogen.

4. The composition of claim 1, wherein $R^1$ is methyl and $R^2$, $R^3$, and $R^4$ are hydrogen.

5. The composition of claim 1, wherein the packaging material is a cardboard container, a plastic container, a wooden box, a paper bag; a wax coating, a coated paper, a plastic film, or an adhesive.

6. The composition of claim 5, wherein the plastic film is polyethylene, ethyl vinylacetate, polyvinyl alcohol or polystyrene.

7. A method to inhibit an ethylene response in a plant comprising the step of enclosing the plant in packaging which incorporates the composition of claim 1.

8. A method to prolong the life of a plant comprising the step of enclosing the plant in packaging which incorporates the composition of claim 1.

9. A method to deliver a cyclopropene compound to a plant comprising the step of enclosing the plant in the composition of claim 1.

10. A article of manufacture comprising the composition of claim 1 enclosed in a water impermeable container.

* * * * *